(12) United States Patent
Wu et al.

(10) Patent No.: US 10,189,867 B2
(45) Date of Patent: Jan. 29, 2019

(54) ORGANOSILICON MODIFIED PHOTOINITIATOR AND A PHOTO-CURABLE ADHESIVE COMPOSITION COMPRISING THE SAME

(71) Applicants: Henkel AG & Co. KGaA, Duesseldorf (DE); Henkel IP & Holding GmbH, Duesseldorf (DE)

(72) Inventors: Hao Wu, Shanghai (CN); Zhiming Li, Shanghai (CN); Jinyou Li, Shanghai (CN); Yong Zhang, Shanghai (CN); Xingang Zhang, Shanghai (CN); Zhixiang Lu, East Lyme, CT (US); Zheng Lu, South Glastonbury, CT (US)

(73) Assignees: Henkel IP & Holding GmbH, Duesselforf (DE); Henkel AG & Co. KGaA, Duesseldorf (DE)

( * ) Notice: Subject to any disclaimer, the term of this patent is extended or adjusted under 35 U.S.C. 154(b) by 0 days.

(21) Appl. No.: 15/443,476

(22) Filed: Feb. 27, 2017

(65) Prior Publication Data

US 2017/0166594 A1 Jun. 15, 2017

Related U.S. Application Data

(63) Continuation of application No. PCT/CN2014/085538, filed on Aug. 29, 2014.

(51) Int. Cl.
*C07F 7/18* (2006.01)
*C08F 4/16* (2006.01)
(Continued)

(52) U.S. Cl.
CPC .............. *C07F 7/1804* (2013.01); *C07F 7/18* (2013.01); *C08F 2/46* (2013.01); *C08F 2/50* (2013.01);
(Continued)

(58) Field of Classification Search
CPC ....... C08F 4/16; C08F 2/50; C08J 3/28; C07F 7/1804; C07F 7/1836
(Continued)

(56) References Cited

U.S. PATENT DOCUMENTS 4,273,907 A 6/1981 Takamizawa et al.
4,391,963 A 7/1983 Shirahata
(Continued)

FOREIGN PATENT DOCUMENTS

CN 1639348 A 7/2005
CN 1668648 A 9/2005
(Continued)

OTHER PUBLICATIONS

Kolar, A. et al., "Photoinitiators With Functional Groups. Part II. Silicon-Containing Photoinitiators", J.M.S.—Pure Appl. Chem., A31(3), pp. 305-318 (1994).
International Search Report for International PCT Patent Application No. PCT/CN2014/085538 dated May 29, 2015.
Kolar, A. et al., "Photoinitiators With Functional Groups. Part II. Silicon-Containing Photoinitiators", J.M.S.—Pure Appl. Chem., A31(3), pp. 305-318 (1994)—Abstract only.
International Search Report for Intonational Application No. PCT/CN2012/085035 dated Sep. 19, 2013.
George A. Olah et al., TrIfluoromethanesutfonic (Triflic) acid catalyzed transformations of a-hydroxy carbonyl compounds. J. Org. Chem., 1991, vol. 56, No. 7, pp. 2531-2534, see line 2 of p. 2534.
Huenig Siegfried et al., Trimethylsilyl cyanide—a reagent for umpolung, XVI. Effect of umpolung moieties on the diastereoselectlyty of the nucleophilic acylation of a-chlral carbonyl compounds, Chemlsche Berlchte, 1989, vol. 122, No. 7, pp. 1329-1339, see compound 6cd in p. 1138.
Xavier Creary et al., Dials-Alder approach to bicydlc a-hydroxy ketones, facile ketol reaarrangements of strained a-hydroxy ketones. J. Org. Chem., 1985. vol. 50, No. 11. pages 1932-1938, see the last but two line in p. 1938.
(Continued)

*Primary Examiner* — Sanza L. McClendon
(74) *Attorney, Agent, or Firm* — James E. Piotrowski

(57) ABSTRACT

The present document discloses an organosilicon modified photoinitiator represented by the general formula (I):

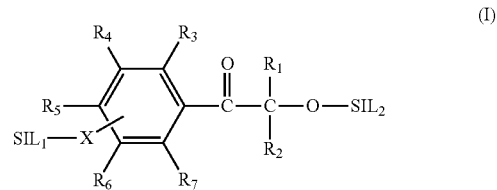

wherein,
$R_1$ and $R_2$ are each independently selected from the group consisting of $C_1$-$C_{20}$ alkyl, $C_2$-$C_8$ alkenyl, $C_5$-$C_8$ cycloalkyl, aryl $C_1$-$C_3$ alkyl;
one of $R_3$, $R_4$, $R_5$, $R_6$, and $R_7$ is SIL1-X, and the others are each independently selected from the group consisting of hydrogen, $C_1$-$C_{20}$ alkyl, $C_2$-$C_8$ alkenyl, $C_5$-$C_8$ cycloalkyl, aryl $C_1$-$C_3$ alkyl, and halogen;
X is a direct bond or $C_1$-$C_{12}$ alkylene; and
SIL1 and SIL2 are each independently represented by the formula —$SiR_8R_9R_{10}$ or $(R'SiO_{3/2})_a(R''_2SiO_{2/2})_b(R'''_3SiO_{1/2})_c$, wherein
$R_8$, $R_9$ and $R_{10}$ are each independently selected from the group consisting of $C_1$-$C_{20}$ alkyl, $C_2$-$C_8$ alkenyl, $C_5$-$C_8$ cycloalkyl, aryl, and aryl $C_1$-$C_3$ alkyl,
R', R" and R''' each independently selected from the group consisting of $C_1$-$C_{20}$ alkyl, $C_2$-$C_8$ alkenyl, $C_5$-$C_8$ cycloalkyl, and phenyl $C_1$-$C_3$ alkyl, and
a, b, and c are numbers that satisfy a≥0, b≥0, c>0, the ratio of a to c is from 0 to 100, and the ratio of b to c is from 0 to 10.

20 Claims, No Drawings

(51) Int. Cl.
- *C08F 2/50* (2006.01)
- *C08F 2/46* (2006.01)
- *C08L 83/04* (2006.01)
- *C08L 83/06* (2006.01)
- *C08F 120/68* (2006.01)
- *C08J 3/28* (2006.01)
- *C09J 133/14* (2006.01)
- *C08G 77/14* (2006.01)

(52) U.S. Cl.
CPC ............... *C08F 120/68* (2013.01); *C08J 3/28* (2013.01); *C08L 83/04* (2013.01); *C08L 83/06* (2013.01); *C09J 133/14* (2013.01); *C08G 77/14* (2013.01); *C08J 2333/14* (2013.01); *C09J 2205/114* (2013.01); *C09J 2433/00* (2013.01)

(58) Field of Classification Search
USPC .......................................................... 522/149
See application file for complete search history.

(56) References Cited

U.S. PATENT DOCUMENTS

| | | | |
|---|---|---|---|
| 4,477,326 A * | 10/1984 | Lin | ........................... C08F 2/50 522/183 |
| 4,507,187 A * | 3/1985 | Jacobine | ................ C08G 77/38 522/35 |
| 4,534,838 A * | 8/1985 | Lin | ........................... C08F 2/50 522/182 |
| 4,536,265 A | 8/1985 | Fabrizio et al. | |
| 4,560,709 A | 12/1985 | Berner et al. | |
| 4,666,953 A * | 5/1987 | Klemarczyk | ............. C08F 2/50 430/281.1 |
| 5,071,936 A * | 12/1991 | Himori | ................ C08G 77/392 525/474 |
| 5,420,222 A * | 5/1995 | Stepp | ....................... C08L 83/04 522/35 |
| 5,663,269 A | 9/1997 | Chu et al. | |
| 5,776,658 A | 7/1998 | Niesert et al. | |
| 5,776,858 A | 7/1998 | Nieserf et al. | |
| 6,376,568 B1 | 4/2002 | Baudin et al. | |
| 6,693,141 B2 | 2/2004 | Baudin et al. | |
| 7,005,281 B2 | 2/2006 | Öhrlein et al. | |
| 7,723,397 B2 | 5/2010 | Hüsler et al. | |
| 9,409,932 B2 | 8/2016 | Li et al. | |
| 9,409,935 B2 * | 8/2016 | Haupfear | ............... C07F 9/3813 |
| 2001/0007880 A1 | 7/2001 | Marchin et al. | |
| 2005/0239971 A1 | 10/2005 | Husler et al. | |

FOREIGN PATENT DOCUMENTS

| | | |
|---|---|---|
| EP | 1072326 A2 | 1/2001 |
| JP | 2008255062 A | 10/2008 |
| WO | 2004009651 A1 | 1/2004 |
| WO | 2014086000 A1 | 6/2014 |

OTHER PUBLICATIONS

James M. Blackwell et al., B(C6F5)3-catalyzed allatlon of alcohols: a mild, general method for synthesis of sityl ethers, J org. Chemc. 1999, vol. 64, No. 13, pp. 4887-4992, see entry 10 in table 2 of p. 4689.

Mitsuru Shindo et al., Heteroatom-guided toreuoselective deflnation of a-oxy and a-amino ketone via ynolatea, Chemistry—A European Journal, 2006, vol. 12, No. 2, pp. 524-536, see compound 8f in table 2 of p. 526.

Holo et al., Manganese Ate Complexes as New Reducing Agents: Perfectly Regiocontrolled Generation and Reactions of the Manganese Enolates with Electrophiles, 1997, J. Am. Chem. Soc., 119, 5459-6450.

Robertson et al., Preparation of sllyl enol ethers from acyloin derivatives using sityllithium reagents. Feb. 6, 2OO8, Tetnahedron Letters, 49, 2088-2090.

Tarr et al., Lanthanum-Tricyanida-Catalyzed Acyl Sllans-Kstona Benzoin Additions and Kinetic Resolution of Resultant alpha-silyloxyketones, Apr. 14, 2010, J. Org. Chem., 75, 3317-3325.

* cited by examiner

ORGANOSILICON MODIFIED PHOTOINITIATOR AND A PHOTO-CURABLE ADHESIVE COMPOSITION COMPRISING THE SAME

TECHNICAL FIELD

The present invention relates to an organosilicon modified photoinitiator and a photo-curable adhesive composition comprising the same.

BACKGROUND

Adhesives used for optically clear display applications, e.g adhesives applied or laminated on a clear display substrate in an electronic assembly, must possess the properties of UV radiation resistance, thermal resistance, hydrolysis resistance, anti-yellowing and low haze. In addition, the photoinitiator which initiates a photo-curing reaction in the photo-curable adhesive composition under exposure to electromagnetic radiation, should possess good compatibility with the other components in the composition and have enough activity to initiate the radical polymerization. Currently, silicone polymers such as organopolysiloxanes are widely used as part of the photo-curable adhesive composition. However, commercially available photoinitiators are not sufficiently compatible or miscible with silicone system. In addition, many commercially available photoinitiators are not stable during or after the radical phot-curing reaction and cause problems such as haze and yellowness of the cured adhesive which are unacceptable especially in the optically clear display application.

U.S. Pat. No. 4,273,907 A discloses an organopolysiloxane modified benzoin based photoinitiator. Regarding practical applications, it has to be mentioned that such benzoin derivatives are only storable for limited time at ambient temperature. Such derivatives tend to be yellowing when exposed to thermal and/or UV radiation.

U.S. Pat. No. 4,536,265 A discloses a siloxane modified acetophenone based photoinitiator. Such acetophenone based photoinitiator also has tendency toward yellowing, and thus is not suitable for use in optically clear display application.

U.S. Pat. No. 5,776,658 A discloses a siloxane modified photoinitiator and photosensitive mixture. It is prepared from benzoin or α-hydroxy-alkylphenones with vinyltrimethoxysilane in the presence of $RuH_2(CO)(PPh_3)_3$ as catalyst. It is reported that the photoinitiator and photosensitive mixture are hydrolytic stable. However, the Ru catalyst is expensive and vinylsiloxane alkylates the aromatic nucleus which is in ortho position to the carbonyl group. The para position is not occupied and could be oxidized, leading to yellowing when exposed to UV radiation.

EP 1072326 A2 discloses a siloxane-containing α-hydroxy-alkylphenones type photoinitiator. The photoinitiators reported in the patent application have a phenyl ether structure. Such structure is unstable under UV radiation and thermal conditions. The ether bond will degrade to phenol structure in harsh conditions and the phenol structure will finally transform to quinonoids which have deep colour and are unacceptable for use in an optically clear display application.

Therefore, it is the object of the present invention to develop an organosilicon modified photoinitiator which can overcome at least one of these challenges. These problems are solved by the disclosed photoinitiators.

SUMMARY OF THE INVENTION

One aspect discloses an organosilicon modified photoinitiator represented by the following formula (I):

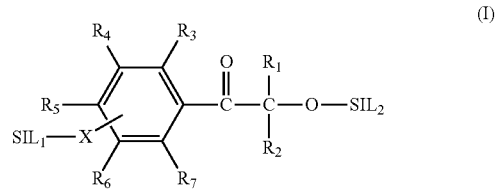

wherein, $R_1$ and $R_2$ are each independently selected from the group consisting of $C_1$-$C_{20}$ alkyl, $C_2$-$C_8$ alkenyl, $C_5$-$C_8$ cycloalkyl, aryl $C_1$-$C_3$ alkyl;

one of $R_3$, $R_4$, $R_5$, $R_6$, and $R_7$ is SIL1-X, and the others are each independently selected from the group consisting of hydrogen, $C_1$-$C_{20}$ alkyl, $C_2$-$C_8$ alkenyl, $C_5$-$C_8$ cycloalkyl, aryl $C_1$-$C_3$ alkyl, and halogen;

X is a direct bond or $C_1$-$C_{12}$ alkylene; and

SIL1 and SIL2 are each independently represented by the formula $-SiR_8R_9R_{10}$ or the formula $(R'SiO_{3/2})_a(R''_2SiO_{2/2})_b(R'''_3SiO_{1/2})_c$, wherein $R_8$, $R_9$ and $R_{10}$ are each independently selected from the group consisting of $C_1$-$C_{20}$ alkyl, $C_2$-$C_8$ alkenyl, $C_5$-$C_8$ cycloalkyl, aryl, and aryl $C_1$-$C_3$ alkyl, R', R'' and R''' each independently selected from the group consisting of $C_1$-$C_{20}$ alkyl, $C_2$-$C_8$ alkenyl, $C_5$-$C_8$ cycloalkyl, and phenyl $C_1$-$C_3$ alkyl, and a, b, and c are numbers that satisfy a≥0, b≥0, c>0, the ratio of a to c is from 0 to 100, and the ratio of b to c is from 0 to 100.

Another aspect discloses a photo-curable composition comprising the above-defined organosilicon modified photoinitiator.

Another aspect discloses use of the above-defined photo-curable composition for bonding or laminating various substrates, and especially in the assembly of optical components, or for bonding or laminating between optically clear substrates or between an optically clear substrate and an opaque substrate.

Another aspect discloses a coated substrate which is coated on at least one surface with the above-defined photo-curable composition.

Another aspect discloses cured reaction products of the above-defined photo-curable composition.

Other features and aspects of the subject matter are set forth in greater detail below.

DETAILED DESCRIPTION

It is to be understood by one of ordinary skill in the art that the present discussion is a description of exemplary embodiments only, and is not intended as limiting the broader aspects of the present invention.

In one aspect, the present disclosure is generally directed to an organosilicon modified photoinitiator represented by the general formula (I):

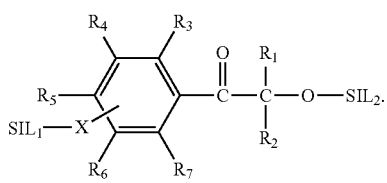

(I)

$R_1$ and $R_2$ are each independently selected from the group consisting of $C_1$-$C_{20}$ alkyl, $C_2$-$C_8$ alkenyl, $C_5$-$C_8$ cycloalkyl, aryl $C_1$-$C_3$ alkyl.

One of $R_3$, $R_4$, $R_5$, $R_6$, and $R_7$ is SIL1-X, and the others are each independently selected from the group consisting of hydrogen, $C_1$-$C_{20}$ alkyl, $C_2$-$C_8$ alkenyl, $C_5$-$C_8$ cycloalkyl, aryl $C_1$-$C_3$ alkyl, and halogen.

X is a direct bond or $C_1$-$C_{12}$ alkylene.

SIL1 and SIL2 are each independently represented by the formula $-SiR_8R_9R_{10}$ or by the formula $(R'SiO_{3/2})_a(R''_2SiO_{2/2})_b(R'''_3SiO_{1/2})_c$.

$R_8$, $R_9$ and $R_{10}$ are each independently selected from the group consisting of $C_1$-$C_{20}$ alkyl, $C_2$-$C_8$ alkenyl, $C_5$-$C_8$ cycloalkyl, aryl and aryl $C_1$-$C_3$ alkyl.

R', R'' and R''' each independently selected from the group consisting of $C_1$-$C_{20}$ alkyl, $C_2$-$C_8$ alkenyl, $C_5$-$C_8$ cycloalkyl, and phenyl $C_1$-$C_3$ alkyl. a, b, and c are numbers that satisfy a≥0, b≥0, c>0, the ratio of a to c is from 0 to 100, and the ratio of b to c is from 0 to 100.

As used herein, $C_1$-$C_{20}$ alkyl refers to a linear or branched moiety containing only single bonds between carbon atoms in the moiety and including, for example, $C_1$-$C_{18}$-, $C_1$-$C_{12}$-, $C_1$-$C_{10}$-, $C_1$-$C_8$-, $C_1$-$C_6$- or $C_1$-$C_4$-alkyl. Examples thereof are methyl, ethyl, propyl, isopropyl, n-butyl, sec-butyl, isobutyl, tert-butyl, pentyl, hexyl, heptyl, 2,4,4-trimethylpentyl, 2-ethylhexyl, octyl, nonyl, decyl, undecyl, dodecyl, hexadecyl, octadecyl and eicosyl.

As used herein, halogen refers to fluorine, chlorine, bromine or iodine, for example fluorine, chlorine or bromine, especially chlorine or fluorine.

As used herein, $C_1$-$C_{12}$ alkylene refers to divalent tethering groups, forming bonds to connect molecular fragments via their terminal carbon atoms and including, for example, methylene ($-CH_2-$), ethylene ($-CH_2CH_2-$), n-propylene ($-CH_2CH_2CH_2-$), isopropylene, n-butylene, sec-butylene, isobutylene, tert-butylene, pentylene, hexylene, heptylene, octylene, nonylene, decylene, undecylene or dodecylene.

As used herein, $C_5$-$C_8$ cycloalkyl refers to linear or branched alkyl containing at least one ring, for example cyclopentyl, methylcyclopentyl, cyclohexyl, methyl- or dimethyl-cyclohexyl or cyclooctyl, especially cyclopentyl and cyclohexyl.

As used herein, $C_2$-$C_8$ alkenyl refers to mono- or polyunsaturated and linear or branched, and is, for example, $C_2$-$C_6$- or $C_2$-$C_4$-alkenyl. Examples thereof are allyl, methallyl, 1,1-dimethylallyl, 1-butenyl, 2-butenyl, 1,3-pentadienyl, 1-hexenyl and 1-octenyl, especially allyl. $R_1$ and $R_2$ as $C_2$-$C_8$ alkenyl are, for example, $C_2$-$C_6$ alkenyl, especially $C_2$-$C_4$ alkenyl.

As used herein, aryl refers to an unsaturated aromatic carbocyclic group of from 6 to 20 carbon atoms having a single ring (e.g., phenyl) or multiple condensed (fused) rings, wherein at least one ring is aromatic (e.g., naphthyl, dihydrophenanthrenyl, fluorenyl, or anthryl). Preferred aryls include phenyl, naphthyl and the like. As used herein, aryl $C_1$-$C_3$ alkyl refers to, for example, benzyl, phenylethyl, α-methylbenzyl or α,α-dimethyl benzyl, especially benzyl.

The above groups may be further substituted or unsubstituted. When substituted, hydrogen atoms on the groups are replaced by substituent group(s) that is(are) one or more group(s) independently selected from alkyl, alkenyl, alkynyl, cycloalkyl, cycloalkenyl, cycloalkynyl, aryl, heteroaryl, heteroalicyclyl, aralkyl, heteroaralkyl, (heteroalicyclyl)alkyl, hydroxy, protected hydroxyl, alkoxy, aryloxy, acyl, ester, mercapto, alkylthio, arylthio, cyano, halogen, carbonyl, thiocarbonyl, O-carbamyl, N-carbamyl, O-thiocarbamyl, N-thiocarbamyl, C-amido, N-amido, S-sulfonamido, N-sulfonamido, C-carboxy, protected C-carboxy, O-carboxy, isocyanato, thiocyanato, isothiocyanato, nitro, silyl, sulfenyl, sulfinyl, sulfonyl, haloalkyl, haloalkoxy, trihalomethanesulfonyl, trihalomethanesulfonamido, and amino, including mono- and di-substituted amino groups, and the protected derivatives thereof. In case that an aryl is substituted, substituents on an aryl group may form a non-aromatic ring fused to the aryl group, including a cycloalkyl, cycloalkenyl, cycloalkynyl, and heterocyclyl.

As used herein, the structure of $(R'SiO_{3/2})_a(R''_2SiO_{2/2})_b(R'''_3SiO_{1/2})_c$ can be identified with reference to certain units contained in a siloxane structure. These units have been designated as M, D, and T units, which represent, respectively, units with the empirical formulae $R'SiO_{3/2}$, $R''_2SiO_{2/2}$, and $R'''_3SiO_{1/2}$, wherein each of R', R'' and R''' represents a monovalent substituent as defined above. The letter designations M, D, T, refer respectively, to the fact that the unit is monofunctional, difunctional, or trifunctional. The units of M, D and T are arranged randomly or in blocks. For example, blocks of units of M, D and T may follow one another, but the individual units may also be linked in random distribution, depending upon the siloxane used during preparation.

In one embodiment, $R_1$ and $R_2$ are each independently selected from the group consisting of $C_1$-$C_{20}$ alkyl, $C_2$-$C_8$ alkenyl, $C_5$-$C_8$ cycloalkyl, aryl, aryl $C_1$-$C_3$ alkyl. In one particular embodiment, $R_1$ and $R_2$ are $C_1$-$C_8$ alkyl, especially $C_1$-$C_6$ alkyl, preferably $C_1$-$C_4$ alkyl, such as methyl, ethyl, n-propyl, iso-propyl, n-butyl, iso-butyl or tert-butyl, especially methyl.

In another embodiment, $R_5$ is SIL1-X, and each of $R_3$, $R_4$, $R_6$, and $R_7$ are hydrogen or $C_1$-$C_8$ alkyl, preferably hydrogen, methyl, ethyl, n-propyl, iso-propyl, n-butyl, iso-butyl, tert-butyl, hexyl, or octyl, especially hydrogen.

In still another embodiment, SIL1 and/or SIL2 is a silyl radical represented by the formula $-SiR_8R_9R_{10}$ where $R_8$, $R_9$ and $R_{10}$ are each independently selected from the group consisting of $C_1$-$C_{20}$ alkyl, $C_2$-$C_8$ alkenyl, $C_5$-$C_8$ cycloalkyl, aryl and aryl $C_1$-$C_3$ alkyl. In one particular embodiment, $R_8$, $R_9$ and $R_{10}$ are each independently $C_1$-$C_8$ alkyl, especially $C_1$-$C_6$ alkyl, preferably $C_1$-$C_4$ alkyl, such as methyl, ethyl, n-propyl, iso-propyl, n-butyl, iso-butyl, tert-butyl, or phenyl or benzyl, especially methyl or benzyl. Preferably, SIL1 and/or SIL2 is selected from the group consisting of trimethylsilyl (TMS), dimethylphenylsilyl, dimethylphenylethylsilyl and tri-n-propylsilyl. In one particular embodiment, $R_8$, $R_9$ and $R_{10}$ are each independently methyl, and SIL1 and/or SIL2 corresponds to trimethylsilyl (TMS). In another particular embodiment, $R_8$ and $R_9$ are each independently methyl, $R_{10}$ is phenyl, and thus SIL1 and/or SIL2 corresponds to dimethylphenylsilyl. In yet another particular embodiment, $R_8$ and $R_9$ are each independently methyl, $R_{10}$ is phenylethyl, and thus SIL1 and/or SIL2 corresponds to dimethylphenylethylsilyl. In yet another particular embodiment, $R_8$, $R_9$ and $R_{10}$ are n-propyl, and thus SIL1 corresponds to tri-n-propylsilyl.

In still another embodiment, SIL1 and/or SIL2 each independently are siloxyl radicals represented by the general formula $(R'SiO_{3/2})_a(R''_2SiO_{2/2})_b(R'''_3SiO_{1/2})_c$, where R', R" and R''' each independently selected from the group consisting of $C_1$-$C_{20}$ alkyl, $C_2$-$C_8$ alkenyl, $C_5$-$C_8$ cycloalkyl, and phenyl $C_1$-$C_3$ alkyl, especially $C_1$-$C_8$ alkyl, preferably $C_1$-$C_6$ alkyl, more preferably $C_1$-$C_4$ alkyl, such as methyl, ethyl, n-propyl or n-butyl, especially methyl; a, b, and c are numbers that satisfy $a \geq 0$, preferably $0 \leq a \leq 5000$, more preferably $0 \leq a \leq 1000$; $b \geq 0$, preferably $0 \leq b \leq 10000$, more preferably $0 \leq b \leq 1000$; $c > 0$, preferably $1 \leq c \leq 5000$, more preferably $1 \leq c \leq 1000$; the ratio of a to c is from 0 to 100, preferably 0 to 50, more preferably 0 to 30; and the ratio of b to c is from 0 to 100, preferably 0 to 80, more preferably 0 to 60. In one particular embodiment, R', R" and R''' each are methyl, and a=0, b=1, and c=2, and accordingly the siloxyl radical corresponds to 1,1,1,3,5,5,5-heptamethyltrisiloxyl. In another particular embodiment, R', R" and R''' each are methyl, and a=0, b=1, and c=3, and accordingly the siloxyl radical corresponds to 1,1,1,5,5,5,7,7,7-nonamethyltetrasiloxyl.

In still another embodiment, the linking group X is a direct bond or $C_1$-$C_{12}$ alkylene, especially $C_1$-$C_8$ alkylene, preferably $C_1$-$C_6$ alkylene, more preferably $C_1$-$C_4$ alkylene, such as methylene, ethylene, n-propylene, iso-propylene, n-butylene, iso-butylene, or tert-butylene, especially a direct bond, methylene, ethylene, or n-propylene.

Especially preferred are the following compounds:

compound of formula (1), wherein $R_1$ and $R_2$ are methyl, $R_5$ is SIL1-X—, in which SIL1 is trimethylsilyl and X is a direct bond, $R_3$, $R_4$, $R_6$ and $R_7$ are hydrogen, and SIL2 is 1,1,1,3,5,5,5-heptamethyltrisiloxyl;

compound of formula (1), wherein $R_1$ and $R_2$ are methyl, $R_5$ is SIL1-X—, in which SIL1 is 1,1,1,3,5,5,5-heptamethyltrisiloxyl and X is ethylene, $R_3$, $R_4$, $R_6$ and $R_7$ are hydrogen, and SIL2 is 1,1,1,3,5,5,5-heptamethyltrisiloxyl;

compound of formula (1), wherein $R_1$ and $R_2$ are methyl, $R_5$ is SIL1-X—, in which SIL1 is 1,1,1,3,5,5,5-heptamethyltrisiloxyl and X is n-propylene, $R_3$, $R_4$, $R_6$ and $R_7$ are hydrogen, X is n-propyl, and SIL2 is 1,1,1,3,5,5,5-heptamethyltrisiloxyl;

compound of formula (1), wherein $R_1$ and $R_2$ are methyl, $R_5$ is SIL1-X—, in which SIL1 is 1,1,1,3,5,5,5,7,7,7-nonamethyltetrasiloxyl and X is ethylene, $R_3$, $R_4$, $R_6$ and $R_7$ are hydrogen, and SIL2 is 1,1,1,3,5,5,5,7,7,7-nonamethyltetrasiloxyl;

compound of formula (1), wherein $R_1$ and $R_2$ are methyl, $R_5$ is SIL1-X—, in which SIL1 is dimethylphenylsilane and X is ethylene, $R_3$, $R_4$, $R_6$ and $R_7$ are hydrogen, and SIL2 is dimethylphenylsilane;

compound of formula (1), wherein $R_1$ and $R_2$ are methyl, $R_5$ is SIL1-X—, in which SIL1 is dimethylbenzylsilane and X is ethylene, $R_3$, $R_4$, $R_6$ and $R_7$ are hydrogen, and SIL2 is dimethylbenzylsilane;

compound of formula (1), wherein $R_1$ and $R_2$ are methyl, $R_5$ is SIL1-X—, in which SIL1 is tri-n-propylsilane and X is ethylene, $R_3$, $R_4$, $R_6$ and $R_7$ are hydrogen, and SIL2 is tri-n-propylsilane;

The following specific compounds are also of special interest as organosilicon modified photoinitiators:

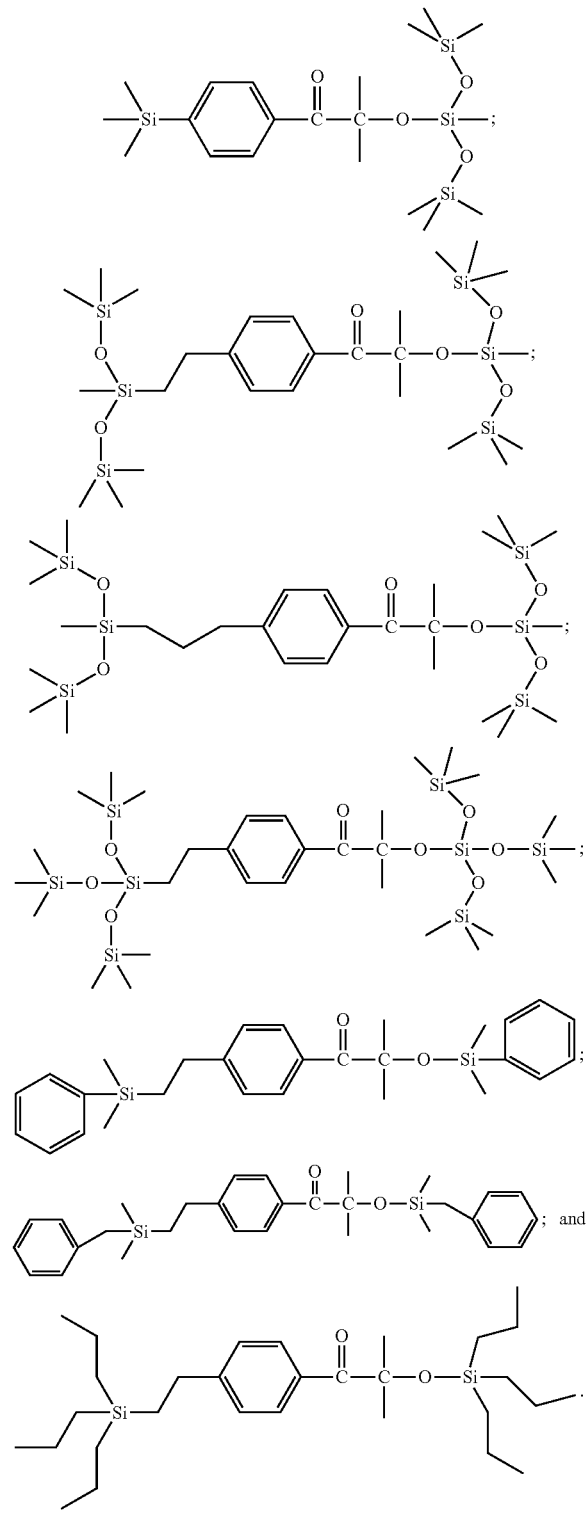

The disclosed organosilicon modified photoinitiator can be prepared by methods known to the person skilled in the art. Typically, the preparation method includes three steps: nucleophilic substitution reaction or hydrosilylation reaction step, nucleophilic addition reaction step and dehydrogenation reaction step as shown in the examples. Suitable processes are disclosed e.g. PCT/CN2012/085935.

Another aspect is directed to a photo-curable composition comprising the organosilicon modified photoinitiator as defined above. In particular, the photo-curable composition comprises: (A) at least one ethylenically unsaturated free-radically photopolymerizable compound; and (B) at least one above-defined organosilicon modified photoinitiator.

The component (A) may contain one or more olefinic double bonds. There is no limitation to the component (A), and the examples of the component (A) and other optional components or additives can be found, for example, in U.S. Pat. No. 6,376,568 B1, which is expressly incorporated herein by reference. In one embodiment the component (A) may be at least one photopolymerizable organopolysiloxane or silicone resin, preferably a (meth)acryloxysiloxane.) The amount of the above-defined organosilicon modified photoinitiator(s) used in the composition is not limited, but for example is within the range of 0.1 to 30% by weight, preferably 0.2 to 15% by weight, based on the total weight of the composition.

Another aspect relates to the use of the above-defined photo-curable composition. The photo-curable composition possesses excellent haze and yellowness, and thus is suitable for bonding or laminating various substrates, and especially in the assembly of optical components, or for bonding or laminating between optically clear substrates or between an optically clear substrate and an opaque substrate.

The present disclosure may be better understood with reference to the following examples.

EXAMPLES

Abbreviation:

Et$_2$O: ethyl ether n-BuLi: n-butyllithium

TMSCl: trimethylsilyl chloride

THF: tetrahydrofuran

TLC: thin layer chromatography

TMS: trimethylsilyl (TMSO)$_2$MeSiH: 1,1,1,3,5,5,5-heptamethyltrisiloxane

Example 1

Synthesis of Photoinitiator PI-1

The photoinitiator PI-1 was synthesized according to Scheme 1 as shown below.

In a 500 mL flask equipped with a thermometer, cooling device and dropping funnel, 1,4-dibromobenzene (23.6 g, 100 mmol) in 200 mL of Et$_2$O was treated with n-BuLi (41.7 mL, 2.4 M in THF) at −78° C., and then the reaction was quenched with TMSCl (5.2 mL, 40 mmol) at −78° C., and IM-1 (22 g, 96% yield) was obtained as oil.

2-hydroxy-2-methylpropanoic acid (10.41 g, 100 mmol) and pyrrolidine (28.4 g, 400 mmol) was coupled in the presence of SOCl$_2$ (14.3 g 120 mmol) in 120 mL toluene and 120 mL THF at −15° C. to −5° C. for 6 h, and 11 g of B-1 was obtained in 70% yield.

In a 100 mL flask equipped with a thermometer, cooling device and dropping funnel, 11 g B-1 was added to a solvent mixture of THF 2 mL and toluene 12 mL. The solution was degassed by vacuum/N$_2$ purge. The mixture was cooled to −35 to −30° C., and n-BuLi (2.4 M in hexane, 2 mL, 4.8 mol) was added slowly over 0.5 h, keeping the temperature below −30° C. In another 100 mL flask equipped with a thermometer, cooling device and dropping funnel, (4-bromophenyl)trimethylsilane (1.0 g, 4.8 mmol) was dissolved in a solvent mixture of THF 2 mL and toluene 12 mL and cooled to −35° C. The solution was also degassed thoroughly. n-BuLi (2.4 M in hexane, 2 mL, 4.8 mol) was added slowly to the cold solution, keeping the temperature below −30° C. The amide-alkoxide solution was transferred into the aryllithium slurry over a 30 min period via cannula. The resulting solution was warmed to −15° C. over 1 h and then to −5° C. over 1 h period. The mixture was aged at −5° C. until the reaction was complete as determined by TLC. The reaction was quenched by aqueous 2N hydrochloric acid with vigorous stirring. This affords 0.620 g (61%) of IM-2 as colorless oil. Scale up also was achieved, and 24 g IM-2 was obtained totally.

Subsequently, 1,1,1,3,5,5,5-heptamethyltrisiloxane (0.485 g 2.18 mmol) and B(C$_6$F$_5$)$_3$ (1.7 mg, 0.0033 mmol) was added to IM-2 (0.90 g, 2.18 mmol) at 60° C. for 30 min. The mixture was then stirred for another 30 min. The reaction mixture was purified by column chromatography on silica column, and 1.0 g PI-1 was obtained. Scale up to give 4.9 g PI-1 totally.

Scheme 1. The preparation of photoinitiator PI-1.

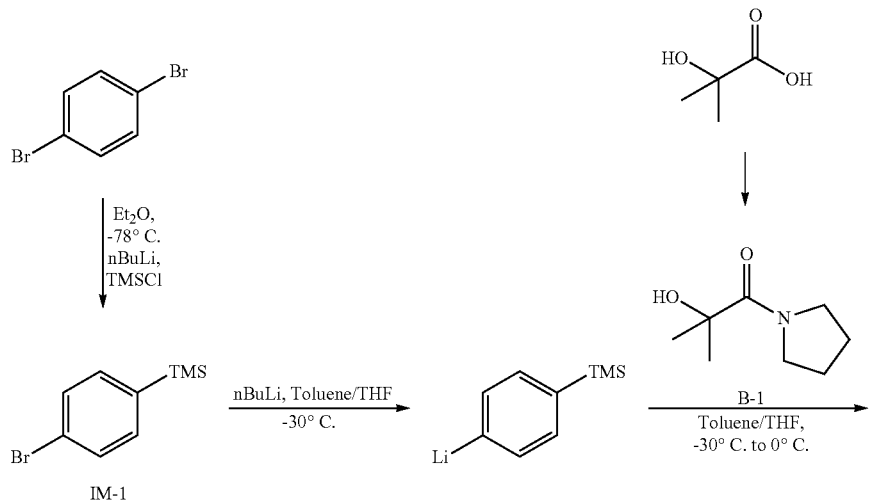

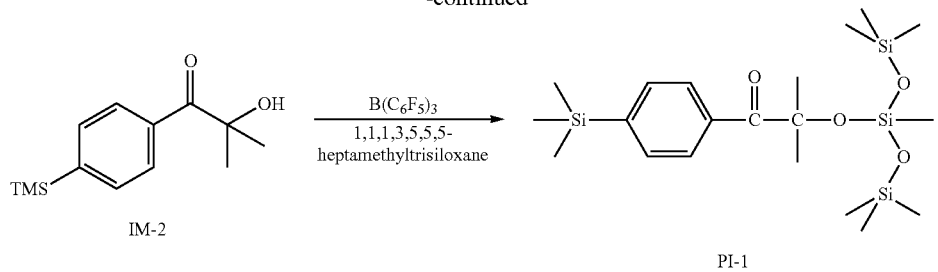

Example 2

Synthesis of Photoinitiator PI-2

The photoinitiator PI-2 was synthesized according to Scheme 2 as shown below. 1-bromo-4-vinylbenzene (183 mg, 1 mmol), toluene (10 mL), 1,1,3,5,5,5-heptamethyltrisiloxane (445 mg, 2 mmol) and platinum(0)-1,3-divinyl-1,1,3,3-tetramethyldisiloxane complex in xylene (2 wt % Pt, 20 μL) were charged in a 50 mL Schlenk tube, then the mixture was heated to 110° C. for 2 days, column chromatography exhibited a complex compound which showed only a pot on TLC plate. Then a large scale of IM-3 1-bromo-4-vinylbenzene (18.3 g) was conducted. The product was used for next step without further purification.

In a 100 mL flask equipped with a thermometer, cooling device and dropping funnel, B-1 (654 mg, 4.2 mg) was added to a solvent mixture of THF 2 mL and toluene 12 mL. The solution was degassed by vacuum/$N_2$ purge. The mixture was cooled to −35 to −30° C. and n-BuLi (1.6 M in hexane, 2.63 mL, 4.2 mol) was added slowly over 0.5 h, keeping the temperature below −30° C. In another 100 mL flask equipped with a thermometer, cooling device and dropping funnel, IM-3 (1.18 g, 5 mmol) was dissolved in toluene 12 ml and THF 2 mL and cooled to −30° C. The solution was also degassed thoroughly. n-BuLi (1.6 M in hexane, 3.12 mL, 5 mol) was added slowly to the cold solution over 2 h to form a white slurry, keeping the temperature below −30° C. The amide-alkoxide solution was transferred into the aryllithium slurry over a 30 min period. The resulting solution was warmed to −15° C. over 1 h and then to −5° C. over 1 h period. The mixture was aged at −5° C. until the reaction was complete as determined by TLC. The reaction was quenched by cannulation into ice-cold aqueous 2N hydrochloric acid with vigorous stirring. This affords 0.9 g of crude IM-4 as oil. Scale up was done to obtain 8.1 g IM-4.

In the next step, 1,1,1,3,5,5,5-heptamethyltrisiloxane (0.485 g 2.18 mmol) and $B(C_6F_5)_3$ (1.7 mg, 0.0033 mmol) was added to IM-4 (0.90 g, 2.18 mmol) at 60° C. for 30 min. then the mixture was stirred for another 30 min. The reaction mixture was purified by column chromatography on silica column to give 1.0 g PI-2. Scale up to give 4.9 g PI-2 totally. $^1$H NMR (400 MHz, $CDCl_3$): 0.01 (m, 6H), 0.1 (m, 36H), 0.82 (m, 2H), 1.58 (m, 6H), 2.65 (m, 2H), 7.03-7.45 (m, 2H), 8.12 (m, 2H).

Scheme 2. The preparation of photoinitiator PI-2.

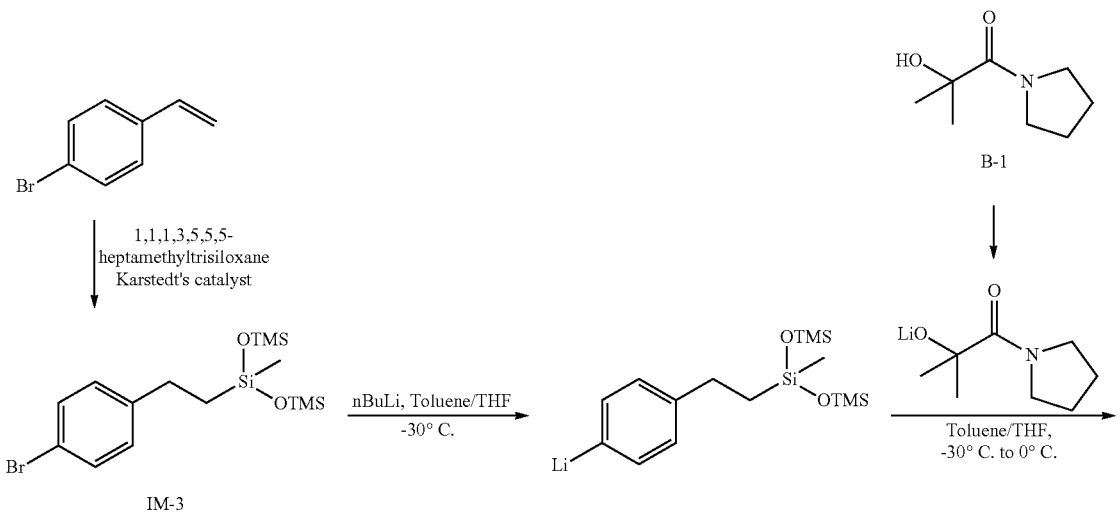

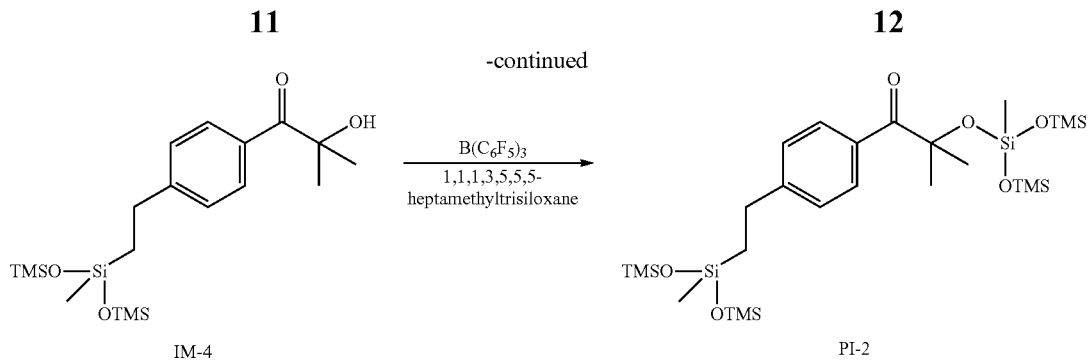

IM-4 → PI-2

Example 3

Synthesis of Photoinitiator PI-3

The photoinitiator PI-3 was synthesized according to Scheme 3 as shown below. In the first step, 1-allyl-4-bromobenzene (7.5 g, 38 mmol), toluene (100 mL), 1,1,3,5,5,5-heptamethyltrisiloxane (12.6 g, 57 mmol) and platinum(0)-1,3-divinyl-1,1,3,3,-tetramethyldisiloxane complex in xylenes (2 wt % Pt, 750 μL) were charged in a 250 mL Schlenk tube, then the mixture was heated to 110° C. for 16 h. The product IM-6 was used for next step without further purification.

In a 100 mL flask equipped with a thermometer, cooling device and dropping funnel, B-1 (1.95 g, 12.4 mg) was added to a solvent mixture of THF 2 mL and toluene 12 mL. The solution was degassed by vacuum/$N_2$ purge. The mixture was cooled to −35 to −30° C. and n-BuLi (2.5 M in hexane, 5.0 mL, 12.4 mmol) was added slowly over 0.5 h, keeping the temperature below −30° C. In another 100 mL flask equipped with a thermometer, cooling device and dropping funnel, IM-5 (5.2 g, 12.4 mmol) was dissolved in toluene 12 ml and THF 2 mL and cooled to −30° C. The solution was also degassed thoroughly. n-BuLi (2.5 M in hexane, 5.0 mL, 12.4 mol) was added slowly to the cold solution over 2 h to form a white slurry, keeping the temperature below −30° C. The amide-alkoxide solution was transferred into the aryllithium slurry over a 30 min period. The resulting solution was warmed to −15° C. over 1 h and then to −5° C. over 1 h period. The mixture was aged at −5° C. until the reaction was complete as determined by TLC. The reaction was quenched by adding dropwise into ice-cold aqueous 2N hydrochloric acid with vigorous stirring. This affords 900 mg of crude IM-6 as oil.

In the next step, 1,1,1,3,5,5,5-heptamethyltrisiloxane (0.485 g 2.18 mmol) and $B(C_6F_5)_3$ (1.7 mg, 0.0033 mmol) was added to IM-6 (0.90 g, 2.18 mmol) at 60° C. for 30 min. The mixture was then stirred for another 30 min. The reaction mixture was purified by column chromatography on silica column, and 1.0 g PI-3 was obtained. Scale up to give 4.9 g PI-3 totally. $^1$H NMR (400 MHz, $CDCl_3$): 0.01 (s, 6H), 0.09 (s, 36H), 0.49 (t, J=9.0 Hz, 2H), 1.61 (s, 6H), 1.64 (m, 2H), 2.67 (t, J=7.5 Hz, 2H), 7.21 (d, J=9.0 Hz, 2H), 8.16 (d, J=9.0 Hz, 2H).

Scheme 3. The preparation of photoinitiator PI-3.

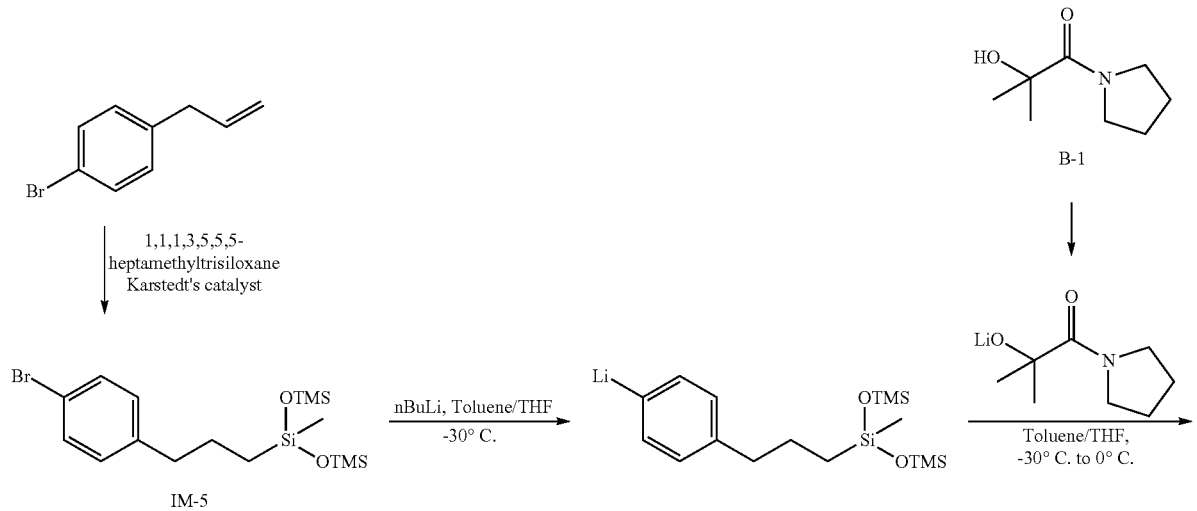

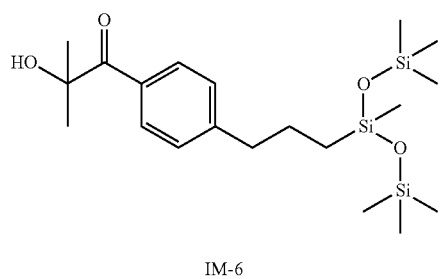

IM-6

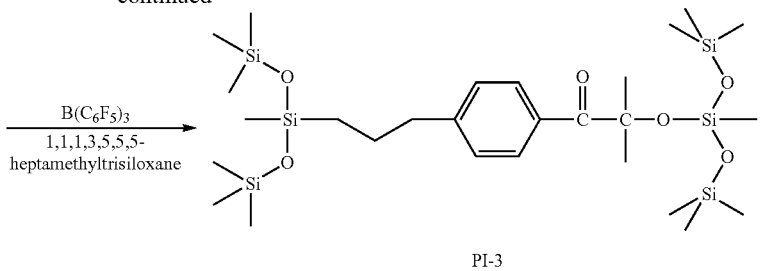

PI-3

Example 4

The Evaluation of Photoinitiators.

PI-2 (E1) was used to evaluate the photo-initiation, UV resistance, anti-yellowing and anti-haze properties. The first comparative example is Darocur® 1173 (CE1), which is especially recommended when UV coatings are required to exhibit only minimal yellowing even after prolonged exposure to sunlight. The second comparative example is IM-4 (CE2), which is silicone mono-substituted in phenyl group only. The third comparative example is PI-0 (CE3), which is silicone mono-substituted in the hydroxyl group of α-hydroxy-alkylphenone. The photoinitiator structures used for evaluation were shown below:

PI-2

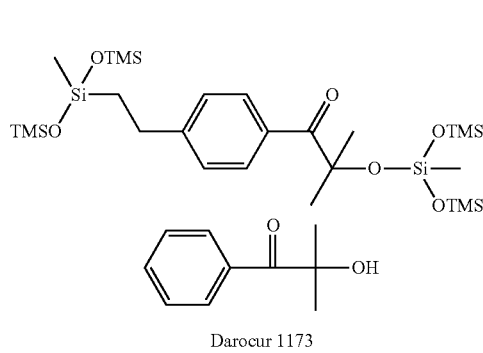

Darocur 1173

PI-0

IM-4

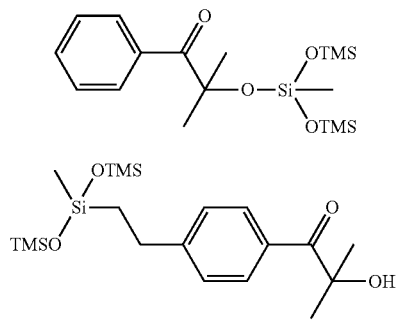

For evaluation, the photoinitiators were homogeneously mixed in acrylate silicone matrix (15MDMA:60DMA=4:1) and exposed to UV radiation respectively. Each amount of the photoinitiators used in the photocurable composition is 1.6 wt % based on the total weight of the adhesive composition.

15MDMA is an acrylate silicone prepared by the reaction of silanol terminated polydimethylsiloxane (Andisil MOH 1000 from AB Specialty Silicones) with methacryloxypropyltrimethoxysilane (Gelest SIA 200.0 from Gelest Inc.) under the presence of lithium n-butyldimethylsilanolate.

60DMA is an acrylate silicone prepared by the reaction of silanol terminated polydimethylsiloxane (Andisil OH 50,000 from AB Specialty Silicones) with methacryloxypropyltrimethoxysilane (Gelest SIA 200.0 from Gelest Inc.) under the presence of lithium n-butyldimethylsilanolate.

Details of the synthesis preparation of 15MDMA and 60DMA are known to a person skilled in the art, and is disclosed in e.g. Example 3 of U.S. Pat. No. 5,663,269.

Each resulting mixture of photoinitiator and polymer was then placed in between 2 layers of glass with an 750 microns air gap to provide a layer of photoinitiator and polymer 750 microns thick, and then subjected to UV irradiation using a Fusion System UV chamber (Producer: Loctite; Type: UVALOC 1000) with an H bulb for 30 seconds at 180 mW/cm$^2$ to cause curing. Immediately after curing, the transmittance, haze and b* value (yellowness) of the samples were measured by a Datacolor 650 apparatus available from Datacolor Corporation according to ASTM D1003, and the result is shown in Table 1. After curing, the composition comprising PI-2 showed lower haze and low b* value compare to those compositions comprising the other comparative photoinitiators. In addition, the cured samples were aged in QUV test machine (UVA-340 available from Q-Lab) for 400 hours. The wavelength region for aging is from 295 nm to 365 nm, and the peak emission is at 340 nm). The transmittance, haze and b* value (yellowness) of the samples were measured again, and the results was shown in Table 1.

TABLE 1

Transmittance, haze and yellowness of the cured products after aging

| | Formulation | Photoinitiator | Transmittance | Haze value | b* value |
|---|---|---|---|---|---|
| CE1 | 15MDMA:60DMA = 4:1 | Darocur ®1173 (1.6 wt %) | 87.01% | 5.7434 | 14.8560 |
| CE2 | 15MDMA:60DMA = 4:1 | PI-0 (1.6 wt %) | 98.74% | 0.5491 | 1.4335 |

TABLE 1-continued

Transmittance, haze and yellowness of the cured products after aging

| | Formulation | Photoinitiator | Transmittance | Haze value | b* value |
|---|---|---|---|---|---|
| CE3 | 15MDMA:60DMA = 4:1 | IM-4 (1.6 wt %) | 98.67% | 7.9374 | 0.9363 |
| E1 | 15MDMA:60DMA = 4:1 | PI-2 (1.6 wt %) | 98.25% | 0.1316 | 0.5338 |

It is well known to a person skilled in the art that the haze value indicates whether the sample is transparent, and the transparency increases as the haze value lowers. In addition, b* value indicates the yellowness of the cured sample, and the tendency to yellowness decreases as the b* value lowers.

As can be seen from Table 1, composition E1 comprising photoinitiator PI-2 exhibited excellent properties in transmittance, haze and b* value and is very suitable for the use in optical clear applications.

Aged comparative sample CE1 initiated by comparative photoinitiator Darocur®1173 exhibited poorer properties in transmittance, haze value and b* value compared to the other samples. Aged comparative sample CE2 initiated by comparative photoinitiator PI-0 exhibited good properties in transmittance and the haze value, but its b* value was significantly larger indicating a yellowness of the aged product. Aged comparative sample CE3 initiated by comparative photoinitiator IM-4 possessed good properties in transmittance and b* value, but its haze* value was considerable. Only the aged sample initiated by inventive photoinitiator PI-2 exhibited an excellent combination of performance in transmittance, haze value and b* value.

Though not wishing to be bound by the following theory, it is assumed that the increased transmittance, haze value and b* value of the aged example initiated by photoinitiator in CE1-3 were caused by the degradation of the photoinitiator during curing and aging processes and the generation of compounds having low molecular weight. Surprisingly, the inventors found that by using the disclosed organosilicon modified photoinitiators, the existence of compounds having low molecular weight during curing and aging in the cured products can be prevented due to the unique structures and design of these photoinitiators.

These and other modifications and variations of the present invention may be practiced by those of ordinary skill in the art, without departing from the spirit and scope of the present invention. In addition, it should be understood that aspects of the various embodiments may be interchanged both in whole or in component. Furthermore, those of ordinary skill in the art will appreciate that the foregoing description is by way of example only, and is not intended to limit the invention so further described in such appended claims.

What is claimed is:

1. An organosilicon modified photoinitiator represented by the general formula (I):

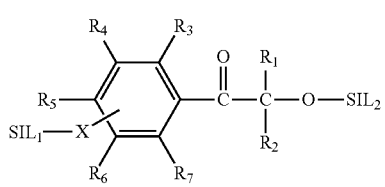

(I)

wherein, $R_1$ and $R_2$ are each independently selected from the group consisting of $C_1$-$C_{20}$ alkyl, $C_2$-$C_8$ alkenyl, $C_5$-$C_8$ cycloalkyl, aryl $C_1$-$C_3$ alkyl;

one of $R_3$, $R_4$, $R_5$, $R_6$, and $R_7$ is SIL1-X, and the others are each independently selected from the group consisting of hydrogen, $C_1$-$C_{20}$ alkyl, $C_2$-$C_8$ alkenyl, $C_5$-$C_8$ cycloalkyl, aryl $C_1$-$C_3$ alkyl, and halogen;

X is a direct bond or $C_1$-$C_{12}$ alkylene; and

SIL1 and SIL2 are each independently represented by the formula —$SiR_8R_9R_{10}$ or $(R'SiO_{3/2})_a(R''_2SiO_{2/2})_b(R'''_3SiO_{1/2})_c$, wherein $R_8$, $R_9$ and $R_{10}$ are each independently selected from the group consisting of $C_1$-$C_{20}$ alkyl, $C_2$-$C_8$ alkenyl, $C_5$-$C_8$ cycloalkyl, aryl, and aryl $C_1$-$C_3$ alkyl, R', R'' and R''' each independently selected from the group consisting of $C_1$-$C_{20}$ alkyl, $C_2$-$C_8$ alkenyl, $C_5$-$C_8$ cycloalkyl, and phenyl $C_1$-$C_3$ alkyl, and a, b, and c are numbers that satisfy a≥0, b≥0, c>0, the ratio of a to c is from 0 to 100, and the ratio of b to c is from 0 to 10.

2. The organosilicon modified photoinitiator according to claim 1, wherein $R_1$ and $R_2$ are $C_1$-$C_4$ alkyl.

3. The organosilicon modified photoinitiator according to claim 1, wherein $R_5$ represents SIL1-X—, and $R_3$, $R_4$, $R_6$, and $R_7$ are each independently selected from the group consisting of hydrogen, $C_1$-$C_4$ alkyl and phenyl $C_1$-$C_3$ alkyl.

4. The organosilicon modified photoinitiator according to claim 1, wherein SIL1 and/or SIL2 is represented by the formula —$SiR_8R_9R_{10}$ where $R_8$, $R_9$ and $R_{10}$ are each independently selected from the group consisting of $C_1$-$C_4$ alkyl, phenyl, and phenyl $C_1$-$C_3$ alkyl.

5. The organosilicon modified photoinitiator according to claim 4, wherein SIL1 and/or SIL2 is selected from the group consisting of trimethylsilyl, dimethylphenylsilyl, dimethylphenylethylsilyl and tri-n-propylsilyl.

6. The organosilicon modified photoinitiator according to claim 1, wherein SIL1 and/or SIL2 is represented by the formula $(R'SiO_{3/2})_a(R''_2SiO_{2/2})_b(R'''_3SiO_{1/2})_c$, wherein R', R'' and R''' are methyl, a=0, b=1, c=2, and SIL1 and/or SIL2 corresponds to 1,1,1,3,5,5,5-heptamethyltrisiloxane.

7. The organosilicon modified photoinitiator according to claim 1, wherein SIL1 and/or SIL2 is represented by the formula $(R'SiO_{3/2})_a(R''_2SiO_{2/2})_b(R'''_3SiO_{1/2})_c$, wherein R', R'' and R''' are methyl, a=0, b=1, c=3, and SIL1 and/or SIL2 corresponds to 1,1,1,3,5,5,5,7,7,7-nonamethyltetrasiloxyl.

8. The organosilicon modified photoinitiator according to claim 1, wherein X is a direct bond or $C_1$-$C_3$ alkylene.

9. The organosilicon modified photoinitiator according to claim 1, wherein $R_1$ and $R_2$ are methyl, $R_5$ is SIL1-X—, in which SIL1 is trimethylsilyl and X is a direct bond, $R_3$, $R_4$, $R_6$ and $R_7$ are hydrogen, and SIL2 is 1,1,1,3,5,5,5-heptamethyltrisiloxyl.

10. The organosilicon modified photoinitiator according to claim 1, wherein $R_1$ and $R_2$ are methyl, $R_5$ is SIL1-X—, in which SIL1 is 1,1,1,3,5,5,5-heptamethyltrisiloxyl and X is ethylene, $R_3$, $R_4$, $R_6$ and $R_7$ are hydrogen, and SIL2 is 1,1,1,3,5,5,5-heptamethyltrisiloxyl.

11. The organosilicon modified photoinitiator according to claim 1, wherein $R_1$ and $R_2$ are methyl, $R_5$ is SIL1-X—, in which SIL1 is 1,1,1,3,5,5,5-heptamethyltrisiloxyl and X is n-propylene, $R_3$, $R_4$, $R_6$ and $R_7$ are hydrogen, X is n-propyl, and SIL2 is 1,1,1,3,5,5,5-heptamethyltrisiloxyl.

12. The organosilicon modified photoinitiator according to claim 1, wherein $R_1$ and $R_2$ are methyl, $R_5$ is SIL1-X—, in which SIL1 is 1,1,1,5,5,5,7,7,7-nonamethyltetrasiloxyl and X is ethylene, $R_3$, $R_4$, $R_6$ and $R_7$ are hydrogen, and SIL2 is 1,1,1,5,5,5,7,7,7-nonamethyltetrasiloxyl.

13. The organosilicon modified photoinitiator according to claim 1, wherein $R_1$ and $R_2$ are methyl, $R_5$ is SIL1-X—, in which SIL1 is dimethylphenylsilane and X is ethylene, $R_3$, $R_4$, $R_6$ and $R_7$ are hydrogen, and SIL2 is dimethylphenylsilane.

14. The organosilicon modified photoinitiator according to claim 1, wherein $R_1$ and $R_2$ are methyl, $R_5$ is SIL1-X—, in which SIL1 is dimethylbenzylsilane and X is ethylene, $R_3$, $R_4$, $R_6$ and $R_7$ are hydrogen, and SIL2 is dimethylbenzylsilane.

15. The organosilicon modified photoinitiator according to claim 1, wherein $R_1$ and $R_2$ are methyl, $R_5$ is SIL1-X—, in which SIL1 is tri-n-propylsilane and X is ethylene, $R_3$, $R_4$, $R_6$ and $R_7$ are hydrogen, and SIL2 is tri-n-propylsilane.

16. A photo-curable composition comprising the organosilicon modified photoinitiator according to claim 1.

17. The photo-curable composition according to claim 16, wherein the amount of the organosilicon modified photoinitiator is 0.5% to 5% by weight, based on the total amount of the composition.

18. A substrate having a surface which is coated on the surface with a photo-curable composition according to claim 17.

19. Cured reaction products of the photo-curable composition according to claim 17.

20. An organosilicon modified photoinitiator, selected from the group consisting of:

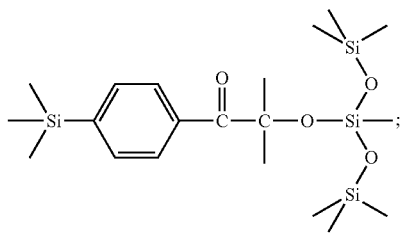

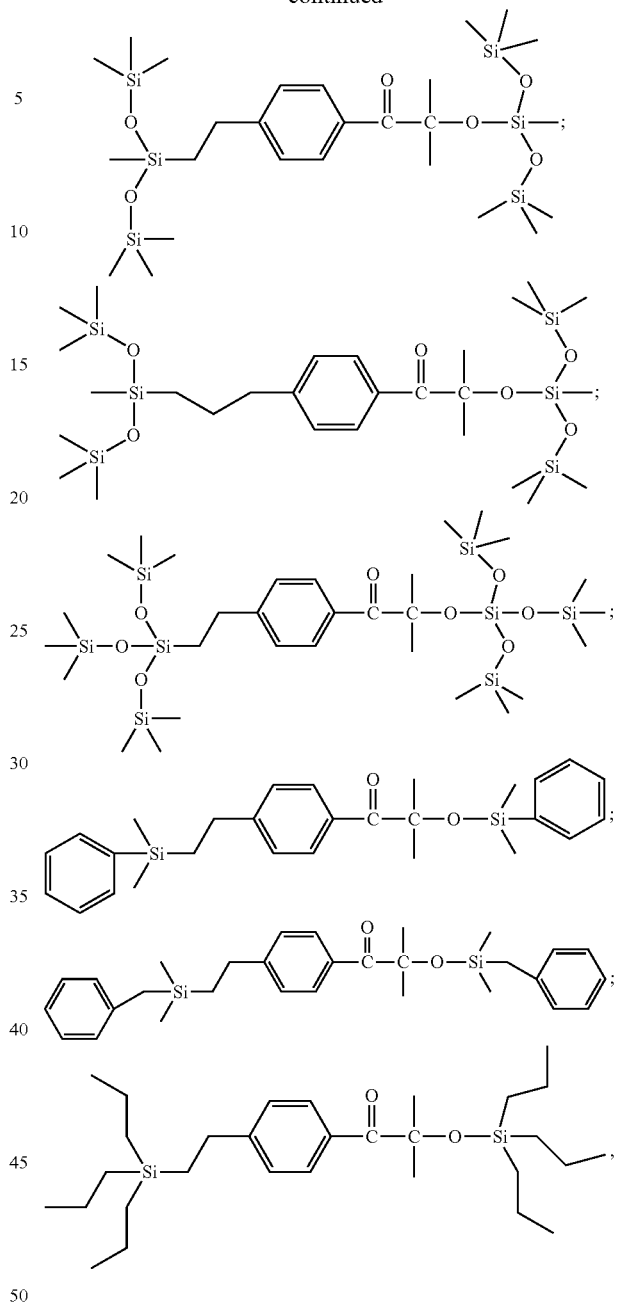

and the combination thereof.